(12) United States Patent
Gransberry et al.

(10) Patent No.: US 12,419,320 B2
(45) Date of Patent: Sep. 23, 2025

(54) FORMULATION TO SOLIDIFY COOKING OIL OR GREASE AND METHODS OF MAKING AND USING THE SAME

(71) Applicant: The Kitchen Laboratories, LLC, Marietta, GA (US)

(72) Inventors: Nao A. Gransberry, Marietta, GA (US); Farris D. Gransberry, Marietta, GA (US)

(73) Assignee: The Kitchen Laboratories, LLC, Marietta, GA (US)

( * ) Notice: Subject to any disclaimer, the term of this patent is extended or adjusted under 35 U.S.C. 154(b) by 63 days.

(21) Appl. No.: 17/850,952

(22) Filed: Jun. 27, 2022

(65) Prior Publication Data

US 2022/0408750 A1 Dec. 29, 2022

Related U.S. Application Data

(60) Provisional application No. 63/216,027, filed on Jun. 29, 2021.

(51) Int. Cl.
| | |
|---|---|
| *A23D 7/05* | (2006.01) |
| *B01J 23/755* | (2006.01) |
| *C07C 69/732* | (2006.01) |
| *C11C 3/04* | (2006.01) |

(52) U.S. Cl.
CPC ............... *A23D 7/05* (2013.01); *B01J 23/755* (2013.01); *C07C 69/732* (2013.01); *C11C 3/04* (2013.01)

(58) Field of Classification Search
CPC ........ A23D 7/05; B01J 23/755; C07C 69/732; C11C 3/04
See application file for complete search history.

(56) References Cited

FOREIGN PATENT DOCUMENTS

KR 101655764 B1 * 9/2016

OTHER PUBLICATIONS

"12 HSA" available online at https://2017erp.com/app/webroot/download/product_techds_pdf/106-14-9_3.pdf (Year: 2017).*

* cited by examiner

*Primary Examiner* — Erik Kashnikow
*Assistant Examiner* — Assaf Zilbering
(74) *Attorney, Agent, or Firm* — Greenberg Traurig, LLP

(57) ABSTRACT

A formulation for solidifying used cooking oil or grease and methods of making and using the same is disclosed. The formulation comprises hydrogenated castor oil, sometimes having a flake morphology. In some embodiments, the formulation has a melting point of between 70 and 80° C. and a density between 0.7 and 1.0 g/L. In some embodiments, the formulation is created by heating castor oil in the presence of a catalyst until at least some of the ricinoleic acid content in the castor oil is reduced to form hydrogenated castor oil in a reaction mixture. The method of using the formulation comprises the steps of mixing the formulation and used cooking oil or grease at an elevated temperature until the formulation completely dissolves into the used cooking oil to form a formulation mixture, and waiting until the formulation mixture cools and solidifies prior to disposal.

7 Claims, 3 Drawing Sheets

FORMULATION TO SOLIDIFY COOKING OIL OR GREASE AND METHODS OF MAKING AND USING THE SAME

CROSS REFERENCE TO RELATED APPLICATIONS

This application claims priority to U.S. provisional patent application Ser. No. 63/216,027, filed on Jun. 29, 2021 to Gransberry et al., entitled "Formulation to Solidify Cooking Oil and Methods of Making and Using the Same", incorporated herein by reference.

TECHNICAL FIELD

The present disclosure is directed to a formulation for used oil or grease disposal, and methods of making and using such formulation.

BACKGROUND

Used cooking oil or grease can be difficult and messy to dispose of. Cooks have long faced compromising choices when dispose used cooking oils or grease. For example, when used cooking oil or grease is disposed down to the sink, not infrequently drain can clog up that is difficult to clean up or fix. Some cooks fill used cooking oil or grease in jars or tubs to throw away, but the process can be tedious and costly, not to mention the mess of broken jars or tubs. If poured directly into trash, used cooking oil or grease can attract flies or other undesirable insects and animals that would negatively affect the hygienic condition of the kitchen or premises. Additionally, some cooking equipment have parts such as dripping pans in oven and air fryer that collects greasy drippings. Disposal of the greasy drippings collected can be messy and time consuming since normally, the equipment parts and collected greasy drippings need to cool down before the disposal process can began. After the removal of the collected greasy drippings, the equipment parts often times needs to be cleaned before next use. There exists a need to dispose used cooking oil or grease more conveniently and efficiently.

SUMMARY

In a first aspect, provided herein is a formulation for solidifying used cooking oil or grease that comprises hydrogenated castor oil. In some embodiments, the formulation has a melting point of between 70 and 80° C. and a density between 0.7 and 1.0 g/L. In some embodiments, the formulation is created by heating castor oil in the presence of a catalyst until at least some of the ricinoleic acid content in the castor oil is reduced to form hydrogenated castor oil in a reaction mixture, treating the reaction mixture with a base followed by an acid to form a second reaction mixture, and drying the second reaction mixture to form the formulation. The ricinoleic acid is known to have a structure of formula formula I

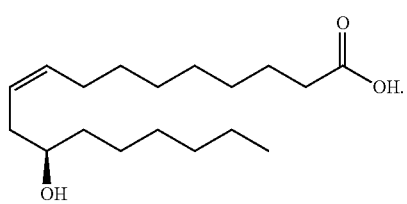

In some embodiments, the formulation has a melting point of about 76° C. and a density of about 0.91 g/L at 85° C. In some embodiments, the catalyst used to make the formulation comprises nickel. In one embodiment, the catalyst comprises nickel and the ratio between the catalyst and the castor oil is about 0.35 g/L. In some embodiments, the castor oil is heated at about 130-150° C. for a total of 8-10 hours in the presence of the catalyst. In some embodiments, the castor oil is heated to about 140° C. in the presence of the catalyst for a total of 8-10 hours until the ricinoleic acid content in castor oil is reduced to form hydrogenated castor oil in the reaction mixture. In some embodiments, the reaction mixture is treated with sodium hydroxide (NaOH) followed by sulfuric Acid ($H_2SO_4$) to form a second reaction mixture and the second mixture is dried to form the formulation in the form of flakes. In one embodiment, the hydrogenated castor oil comprises 12-hydroxy steric acid (Formula II)

formula II

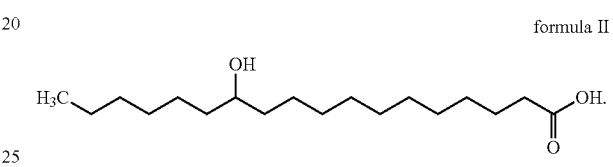

In a second aspect, provided herein is a method of using the formulation disclosed herein. The method comprises the steps of mixing the formulation and used cooking oil or grease at an elevated temperature until the formulation completely dissolves into the used cooking oil to form a formulation mixture, and waiting until the formulation mixture cools and solidifies prior to disposal. In some embodiment, the ratio between the formulation and the used cooking oil is 0.7-1.3 g of the formulation per 20-30 mL of the used cooking oil. In one embodiment, the ratio between the formulation and the used cooking oil is about 1 g of the formulation per 25 mL of the used cooking oil.

In a third aspect, provided herein is a method of making a formulation for solidifying used cooking oil, the formulation comprising hydrogenated castor oil and the formulation having a melting point of between 70 and 80° C. and a density of between 0.7 and 1.0 g/L. In some embodiments, the method comprises heating castor oil in the presence of a catalyst at about 130-150° C. for a total of 8-10 hours until at least some of the ricinoleic acid content in the castor oil is reduced to form hydrogenated castor oil in a reaction mixture, treating the reaction mixture with a base followed by an acid to form a second reaction mixture, and drying the second reaction mixture to form the formulation. In one embodiment, the ratio between the catalyst and the castor oil is about 0.1-1.0 g/L. In some embodiments, the catalyst comprises nickel. In one embodiment, the catalyst comprises nickel and the ratio between the catalyst and the castor oil is about 0.35 g/L. In one embodiment, the castor oil is heated to about 140° C. in the presence of the catalyst for a total of 8-10 hours until the ricinoleic acid content in castor oil is reduced to form hydrogenated castor oil in a reaction mixture. In one embodiment, the reaction mixture is treated with sodium hydroxide (NaOH) followed by sulfuric Acid ($H_2SO_4$) to form a second reaction mixture. In one embodiment, the second mixture is dried to form the formulation in the form of flakes.

BRIEF DESCRIPTION OF THE DRAWINGS

The drawing figures disclosed herein are not necessarily to scale, and certain features may be shown exaggerated in scale or in a somewhat generalized or schematic form in the interest of clarity and conciseness. For more complete understanding of the features and advantages of the present invention, reference is now made to the detailed description of the invention along with the accompanying figures.

Figure 1:
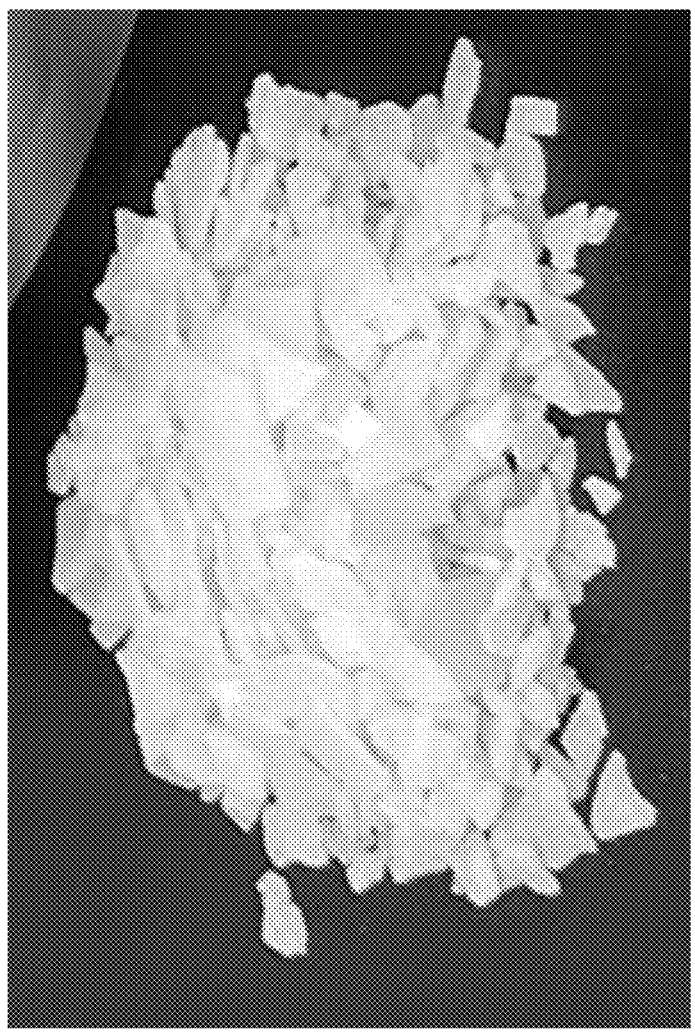
FIG. 1 shows the formulation disclosed herein in flake morphology.

Additional features will be set forth in part in the description which follows, and in part will become apparent to those skilled in the art upon examination of the accompanying drawings or may be learned by production or operation of the examples. The features of the present disclosure may be realized and attained by practice or use of various aspects of the methodologies, formulations. and combinations set forth in the detailed descriptions and examples discussed below.

DETAILED DESCRIPTION

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terms "a" and "an" are defined as one or more unless this disclosure explicitly requires otherwise. The term "substantially" is defined as largely but not necessarily wholly what is specified (and includes what is specified, e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a composition or formulation that "comprises," "has," "includes" or "contains" one or more elements possesses those one or more elements but is not limited to possessing only those elements. Likewise, a method that "comprises," "has," "includes" or "contains" one or more steps possesses those one or more steps but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

"Amount effective" and "effective amount" in the context of a formulation for oil or grease disposal refers to an amount of the formulation that produces solids at room temperature, for example, after dissolved in used cooking oil. Therefore, in some embodiments, an amount effective is any amount of a formulation provided herein that produces one or more of these desired responses. The amount is one that a user believes to solidify a given amount of used cooking oil or grease.

Disclosed herein is a formulation to conveniently dispose of used cooking oil or grease by transforming used cooking oil or grease into a gelatinous solid that can easily be tossed in the trash, and methods of making and using such formulation. The formulation disclosed herein is a plant-based cooking oil solidifier that utilizes natural, sustainable, and non-toxic ingredients. The formulation disclosed herein makes it easy to turn unwieldy, hot oil slurry into a gelatinous solid that can be thrown into the garbage by combining the formulation with used cooking oil or grease at elevated temperature to form a mixture and wait for a period of time until the mixture solidifies.

The active ingredient of the formulation comprises hydrogenated castor oil that is created by hydrolyzing castor oil to remove at least some of its ricinoleic acid at a particular temperature. In some embodiments, castor oil is heated to about 130-150° C. for a total of 8-10 hours in the presence of a catalyst to form hydrogenated castor oil in a reaction mixture. For example, in one embodiment, castor oil is heated to about 140° C. for a total of 8-10 hours in the presence of a catalyst to form hydrogenated castor oil. In some embodiments, the method of making the formulation further comprises treating the reaction mixture with a base followed by an acid to form a second reaction mixture, and drying the second reaction mixture to form the formulation. In some embodiments, the base used to treat the reaction mixture is an inorganic base such as sodium hydroxide (NaOH) or alike. In some embodiments, the base used to treat the reaction mixture is an inorganic acid such as sulfuric acid ($H_2SO_4$) or alike. In one embodiment, the reaction mixture is treated with sodium hydroxide (NaOH) followed by sulfuric acid ($H_2SO_4$) to form a second reaction mixture and the second mixture is dried to form the formulation in the form of flakes, such as those shown in FIG. 1. In some embodiments, the concentration of the NaOH used is between 10 to 50%, such as between 10-15%, 15-20%, 20-25%, 25-30%, 30-35%, 35-40%, 40-45%, or 45-50%. In some embodiments, the concentration of the $H_2SO_4$ used is between 15 to 65%, such as between 15-20%, 20-25%, 25-30%, 30-35%, 35-40%, 40-45%, 45-50%, 50-55%, 55-60%, or 60-65%. In one embodiment, the concentration of the NaOH used is 30%. In one embodiment, the concentration of the $H_2SO_4$ used is 40%.

In one embodiment, the catalyst comprises nickel. In some embodiments, the ratio between the catalyst and the castor oil is about 0.1-1.0 g/L, such as 0.1-0.2 g/L, 0.2-0.3 g/L, 0.3-0.4 g/L, 0.4-0.5 g/L, 0.5-0.6 g/L, 0.6-0.7 g/L, 0.7-0.8 g/L, 0.8-0.9 g/L, or 0.9-1.0 g/L. In one embodiment, the catalyst comprises nickel and the ratio between the catalyst and the castor oil is about 0.35 g/L. In one embodiment, the main component of the hydrogenated castor oil is 12-hydroxy stearic acid and it is formed by hydrogenation of ricinoleic acid present in the castor oil. In one embodiment, there is about 10%, 8%, 5%, 2%, 1%, 0.5%, 0.2%, or 0.1% unreacted ricinoleic acid left in the hydrogenated castor oil in the formulation.

In general, the formulation disclosed herein has a melting point of between 70 and 80° C. such as between 70 and 71° C., 71 and 72° C., 72 and 73° C., 73 and 74° C., 74 and 75° C., 75 and 76° C., 76 and 77° C., 77 and 78° C., 78 and 79° C., or 79 and 80° C. and a density between 0.7 and 1.0 g/L such as between 0.7 and 0.75 g/L, 0.75 and 0.8 g/L, 0.8 and 0.85 g/L, 0.85 and 0.9 g/L, 0.9 and 0.95 g/L, or 0.95 and 1.0 g/L. In one embodiment, the formulation disclosed herein has a melting point of about 76° C. and a density of about 0.91 g/L at 85° C.

Disclosed herein is a method of using the formulation. The method comprises mixing the formulation and used cooking oil or grease at an elevated temperature until the formulation completely dissolves into the used cooking oil or grease to form a formulation mixture, and waiting until the formulation mixture cools and solidifies prior to disposal. Examples of elevated temperature including, 50° C. and higher, 55° C. and higher, 60° C. and higher, 65° C. and higher, 70° C. and higher, 75° C. and higher, 80° C. and higher, 85° C. and higher, 90° C. and higher, 95° C. and higher, 100° C. and higher, 105° C. and higher, 110° C. and higher, 115° C. and higher, or 120° C. and higher.

In general, the ratio between the formulation and the used cooking oil is 0.7-1.3 g of the formulation such as 0.7-0.8 g, 0.8-0.9 g, 0.9-1.0 g, 1.0-1.1 g, 1.1-1.2 g, or 1.2-1.3 g, per 20-30 mL of the used cooking oil or grease, such as 20-21 mL, 21-22 mL, 22-23 mL, 23-24 mL, 24-25 mL, 25-26 mL, 26-27 mL, 27-28 mL, 28-29 mL, or 29-30 mL. In one embodiment, the ratio between the formulation and the used cooking oil is about 1 g of the formulation per 25 mL of the used cooking oil or grease.

In some embodiments of any of the formulations and methods provided, the effective amount is one in which the used cooking oil is solidified, by waiting for at least 10 min, at least 20 min, at least 30 min, at least 40 min, at least 50 min, at least 60 min, at least 70 min, at least 80 min, at least 90 min, at least 100 min, or longer, after the formulation disclosed herein is dissolved in used cooking oil or grease.

Effective amount will depend, of course, on the composition of the used cooking oil to be solidified; the duration of the treatment; the concentration of the formulation, and the specific method of treatment or application. The effective amount can be 1 scoop of the formulation for every cup of cooking oil, for example, 0.1-0.2 scoop of the formulation for every cup of used cooking oil, 0.2-0.3 scoop of the formulation for every cup of used cooking oil, 0.3-0.4 scoop of the formulation for every cup of used cooking oil, 0.4-0.5 scoop of the formulation for every cup of used cooking oil, 0.5-0.6 scoop of the formulation for every cup of used cooking oil, 0.6-0.7 scoop of the formulation for every cup of used cooking oil, 0.7-0.8 scoop of the formulation for every cup of used cooking oil, 0.8-0.9 scoop of the formulation for every cup of used cooking oil, 0.9-1 scoop of the formulation for every cup of used cooking oil, 1-2 scoop of the formulation for every cup of used cooking oil, 2-3 scoop of the formulation for every cup of used cooking oil, 3-4 scoop of the formulation for every cup of used cooking oil, 4-5 scoop of the formulation for every cup of used cooking oil, or 5-6 scoop of the formulation for every cup of used cooking oil. One scoop of the formulation equals to about 10 g. And one cup of the cooking oil equals to about 250 mL.

Figure 3B:
FIG. 3B shows the back side of the package of FIG. 3A.
Figure 3A:
FIG. 3A shows the front side of a package containing the formulation disclosed herein in flake morphology along with a scoop for measuring and dispensing the formulation contained in the package.

As shown in FIGS. 3A and 3B, the formulation disclosed herein may be packaged in a resealable bag along with a scoop for the ease of dispensing the formulation, with the back of the resealable bag printed with instructions of how to use the formulation to dispose of used cooking oil or grease.

Disclosed herein is a method of using the formulation to dispose oil or grease in an equipment such as a dripping pan in an oven or air fryer. In some embodiments, the method comprises the steps of sprinkling the formulation on a bottom tray of an oven or air fryer; using the oven or air fryer to cook a food on a rack above the bottom tray to allow the formulation in the bottom tray to dissolve and catch drippings from the food to form a formulation mixture; and allowing the formulation mixture to cool and solidify prior to disposal. In some embodiments, the ratio between the formulation and the dripping is 0.7-1.3 g of the formulation per 2-30 g of dripping. In some embodiments, the ratio between the formulation and the dripping is about more than 1 g of formulation to 5-25 milliliter or gram of dripping.

Throughout this application, various publications may be referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

The present disclosure may be understood more readily by reference to the following detailed description of embodiments and to the Figures and their previous and following description.

EXAMPLES

Example 1 Method of Making the Formulation

Reagents and Materials
1. castor oil containing ricinoleic acid (formula I)

formula I 2. nickel catalyst
3. NaOH having a concentration of 30%
4. $H_2SO_4$ having a concentration of 40%

Formulation Preparation

Castor oil is heated to 140+/−2° C. for a total of 8-10 hours until the ricinoleic acid content in castor oil is reduced to form hydrogenated castor oil in a reaction mixture. The reaction mixture is treated with NaOH followed by $H_2SO_4$ and dried to form the formulation in the form of flakes that contains 12-hydroxy steric acid (Formula II).

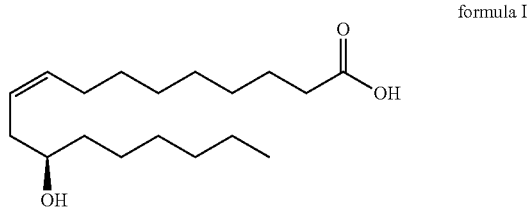 [SMILES: CCCCCC[C@@H](O)C/C=C\CCCCCCCC(=O)O]

formula II

The formulation thus formed has a melting point of 76° C., which at 85° C., has a density of 0.91 grams per liter.

Example 2 Method of Using the Formulation

Figure 2:
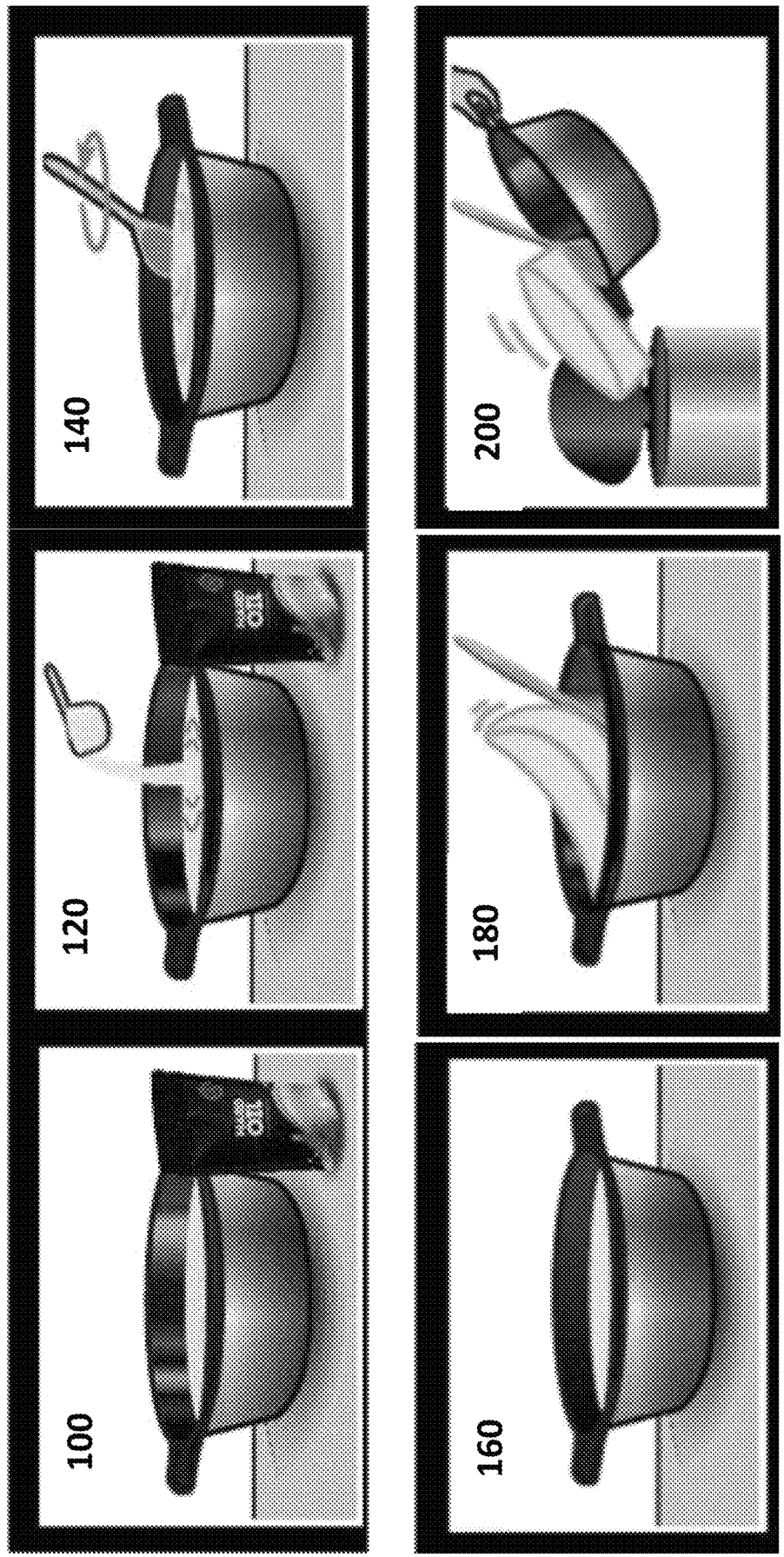
FIG. 2 shows the process of using the formulation disclosed herein to dispose used cooking oil.

The formulation of Example 1 is then used to solidify cooking oil using the following steps, which are illustrated in FIG. 2:

In step 100: after using cooking oil, remove it from heat source such as fire, electronic fryer etc.

In step 120: pour 1 scoop or about 10 grams of the formulation into every cup or about 250 mL used of cooking oil while the oil is still hot, for example, at about 176 F or 80° C. and above. Increase the amount of formulation used, for example using two scoops or three scoops of the formulation for every cup of used cooking oil, if heavy breading or batter is present in the used cooking oil.

In step 140: Mix the formulation and the used cooking oil together until the formulation completely dissolves into the used cooking oil.

In step 160: Wait approximately 1 hour until the used cooking oil completely cools or drop below 40° C. to a solid state. Larger pot or fryers may require longer cooling time.

In step 180: To discard, first release the solidified oil from the surface of the pot by sliding a spatula along the edge.

In step 200: Dispose of the solidified used cooking oil in the trash.

The embodiments above are intended to be illustrative and not limiting. Additional embodiments are within the claims. In addition, although the present disclosure has been described with reference to particular embodiments, those skilled in the art will recognize that changes can be made in form and detail without departing from the spirit and scope of the disclosure. Any incorporation by reference of documents above is limited such that no subject matter is incorporated that is contrary to the explicit disclosure herein.

We claim:

1. A formulation for solidifying used cooking oil, comprising hydrogenated castor oil,
   wherein the formulation is created by:
   heating castor oil at about 130-150° C. for 8-10 hours in the presence of a catalyst until at least some of the ricinoleic acid content in the castor oil is reduced to form hydrogenated castor oil in a reaction mixture, wherein the ratio between the catalyst and the castor oil is about 0.1-1.0 g/L, treating the reaction mixture with a base followed by an acid to form a second reaction mixture, and
   drying the second reaction mixture to form flakes of the formulation,
   wherein the ricinoleic acid has a structure of formula I

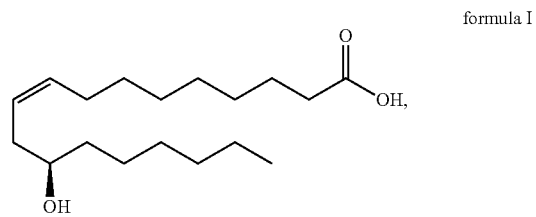 [SMILES: CCCCCC[C@@H](O)C/C=C\CCCCCCCC(=O)O]

formula I and
wherein the formulation has a melting point of between 7° and 80° C. and a density between 0.7 and 1.0 g/L.

2. The formulation of claim 1, wherein the formulation has a melting point of about 76° C. and a density of about 0.91 g/L at 85° C.

3. The formulation of claim 1, wherein the catalyst comprises nickel.

4. The formulation of claim 1, wherein the catalyst comprises nickel and the ratio between the catalyst and the castor oil is about 0.35 g/L.

5. The formulation of claim 1, wherein the castor oil is heated to about 140° C. in the presence of the catalyst for a total of 8-10 hours.

6. The formulation of claim 1, wherein the reaction mixture is treated with sodium hydroxide (NaOH) followed by sulfuric acid ($H_2SO_4$) to form a second reaction mixture.

7. The formulation of claim 1, wherein the hydrogenated castor oil comprises 12-hydroxy steric acid (Formula II)

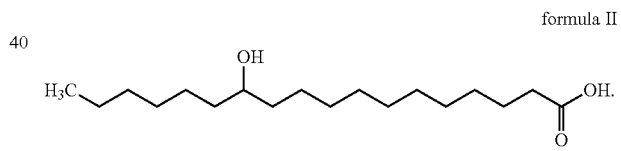

formula II

* * * * *